(12) United States Patent
Gardner et al.

(10) Patent No.: US 8,469,033 B2
(45) Date of Patent: Jun. 25, 2013

(54) LIMB SUPPORT

(75) Inventors: Andrew Gardner, Malvern (GB); Petrus Van Der Walt, Barnstaple (GB)

(73) Assignee: The Malvern Orthopaedic Company Ltd, Malvern (GB)

(*) Notice: Subject to any disclaimer, the term of this patent is extended or adjusted under 35 U.S.C. 154(b) by 436 days.

(21) Appl. No.: 12/517,486

(22) PCT Filed: Dec. 5, 2007

(86) PCT No.: PCT/GB2007/004667
§ 371 (c)(1),
(2), (4) Date: Dec. 8, 2009

(87) PCT Pub. No.: WO2008/068489
PCT Pub. Date: Jun. 12, 2008

(65) Prior Publication Data
US 2010/0089407 A1    Apr. 15, 2010

(30) Foreign Application Priority Data
Dec. 5, 2006 (GB) .................................. 0624228.3

(51) Int. Cl.
*A61F 5/37* (2006.01)
(52) U.S. Cl.
USPC ......................................... 128/882; 128/845

(58) Field of Classification Search
USPC ................................................ 128/845, 882
See application file for complete search history.

(56) References Cited

U.S. PATENT DOCUMENTS

| 830,776 | A | * | 9/1906 | Flagg | ................................ | 5/648 |
| 2,581,110 | A | | 1/1952 | Kenworthy | | |
| 3,653,378 | A | | 4/1972 | Reuther | | |
| 4,265,232 | A | * | 5/1981 | Stonich | ............................. | 5/647 |

FOREIGN PATENT DOCUMENTS

| GB | 159 422 A | 3/1921 |
| GB | 2 253 565 A | 9/1992 |

OTHER PUBLICATIONS

International Search Report related to PCT/GB2007/004667.

* cited by examiner

*Primary Examiner* — Patricia Bianco
*Assistant Examiner* — Camtu Nguyen
(74) *Attorney, Agent, or Firm* — Husch Blackwell LLP (57) ABSTRACT

A limb support comprising a first portion for supporting the lower part of a patient's lower limb, a second portion for supporting the upper part of the patient's lower limb, each portion with deep guttering suitable for providing rotational and angulatory support to the portion of the limb, an adjustable support, and surface engaging portions comprising the adjustable support and free end of the second portion.

16 Claims, 10 Drawing Sheets

LIMB SUPPORT

This invention relates to a lower limb support, which has particular application to support after lower limb injury or surgery.

After lower limb injury or surgery, swelling and deep vein thrombosis are not infrequent complications. Swelling can contribute to the development of stiffness, skin breakdown, infection or compromise of the circulation with potentially disastrous consequences. Deep vein thrombosis can lead to potential fatal pulmonary embolism (blood clot to the lung).

A range of lower extremity injuries often require some days of elevation before definitive surgery can be safely considered, due to the nature of the injury or degree of swelling. Effective elevation after significant lower limb trauma surgery is in most cases desirable. Rotational and/or angulatory control during this time is usually helpful. Although most adult and a significant percentage of paediatric femur fractures are now treated by surgical stabilisation and not in traction for several weeks as previously, a percentage of femur and hip injuries and other conditions, are still treated in traction for a range of reasons. Elevation with rotational and angulatory control is usually desirable in such cases.

Currently used lower limb supports are either rather basic or excessively complex. The foot end of the patient's bed can be elevated, but the upper body and head of the patient then usually also needs elevation, leaving the pelvis, another area well known for the development of even more serious clots in the larger veins, as the lowest point, and therefore at risk. The commonest form of lower limb elevation in most hospitals is still the use of one or more pillows, since this solution is inexpensive, comfortable and always available. The use of one or more pillows is however unstable and unreliable when more than slight elevation is desirable. Further, it cannot provide rotational or angulatory support, which is often necessary. A range of foam wedges for elevation and a foam gutter to control rotation are available. These are, however, bulky, often not supportive enough to control rotation or angulation, and not adjustable. Rigid metal frames are used in many hospitals, but these do not provide rotational or angulatory support and are usually not adjustable.

An object of the invention is to provide in an improved manner a limb support for the elevation thereof.

According to a first aspect of the invention there is provided a limb support comprising a first portion for supporting the lower part of a patient's lower limb, a second portion for supporting the upper part of the patient's lower limb, a support for supporting the first portion above a surface, in use, and adjustable locking hinge means connecting the first and second portions together.

Preferably each of the first and second portions is open-topped, and more preferably they are contoured to support said lower and upper parts of the patient's lower limb respectively.

Desirably each of the first and second portions are internally padded. The padding can be removable so that different thickness can be used for different sizes of limb, and can thus be a disposable item. The portions may also have a disposable cover therein. Conveniently the second portion is provided internally with side support for the patient's knee. Advantageously the end of the second portion remote from its connection to the first portion has its edge tapered to accommodate the patient's thigh. Moreover at said end, the sides of the second portion are sloped to reduce in height to said tapered edge.

In a preferred embodiment the internal surface of the first portion is longitudinally centrally recessed to accommodate, in use, the patient's heel. Preferably at the end of the first portion adjacent its connection to the second portion, the sides of the first portion are reduced to accommodate, in use, a tibial or traction pin in the lower part of the patient's lower limb.

Conveniently the locking hinge means comprise first and second interengaging parts associated with the first and second portions respectively. In a preferred embodiment the locking hinge means comprise first and second interengaging castellated plates. One of the plates is preferably directly fixed to its associated limb support portion, whilst the other of the plates is part of an adjustment bracket or link adjustably connectable with the other of the limb support portions. The bracket or link can be slidably adjustable relative to said other of the limb support portions, and the adjustment could be stepped or alternatively it could be stepless.

In the most preferred embodiment, a pair of said first and second interengaging parts is provided at each side of the limb support to connect the first and second parts together.

Advantageously the support for supporting the first portion above a surface, in use, is in the form of a stirrup, the opposite free ends of which are connected at respective opposite external sides of the first portion. In a preferred embodiment the stirrup is carried by a base structure resting, in use, on said surface. The base structure can be vertically adjustable, and in a most preferred embodiment, each connection between a free end of the stirrup and a side of the first portion of the limb support is in the form of an adjustable locking hinge, which may be of the type comprising interengaging castellated plates, i.e. of the same type connecting the first and second portions of the limb support.

The base structure may comprise a single vertically adjustable, upright disposed centrally of the stirrup, or it may comprise a pair of spaced uprights disposed symmetrically of the stirrup, each possibly vertically adjustable. The single upright, or the pair of uprights may extend to a transverse foot bar or the like received, in use, on said surface.

According to a second aspect of the present invention, there is provided a limb support comprising a first portion for supporting the lower part of a patient's lower limb, a second portion for supporting the upper part of the patient's lower limb, the first and second portions being pivotally connected together, and a base structure having a first part to which the first portion is pivoted, and a second part to which the second portion is pivoted, the length of the base structure defined by said first and second parts being adjustable to alter the degree of elevation/inclination of at least one of the first and second portions.

Preferably each of the first and second portions is open-topped, and more preferably they are contoured to support said lower and upper parts of the patient's lower limb respectively. The end of said first portion remote from said second portion may be closed.

Desirably the first and second parts of the base structure are telescopically slidably adjustable to alter the length of the base structure and thus the respective elevations/inclinations of the first and second support portions. In one embodiment the first part has one or more upstanding arms at or between which is a crossbar to which said first portion is pivoted. The upstanding arm or arms can be length adjustable.

The second part of the base structure advantageously is slidable within hollow tubes of the first part of the base structure, and conveniently said second portion is pivoted to a crossbar of said second part of the base structure. More desirably locking means are provided for locking the base structure in a selected adjusted position and for releasing same when adjustment is required. In one embodiment the adjustment is stepless, but alternatively the locking means could engage in spaced longitudinal openings to provide stepped adjustment. The locking means can be one or more lock nuts, or alternatively one or more over-centre clamps or levers for a quick lock and release.

The first and second support portions are preferably pivotally connected together by a pair of pivots at respective opposite sides thereof, each pivot preferably being made up of a part connected to the first portion and a part connected to the second portion. More preferably each connection is by means of a link riveted or otherwise secured to the first or second portion.

Each of the first and second support portions are preferably internally padded. The padding can be removable so that different thicknesses can be used for different sizes of limb, and can thus be a disposable item.

Other aspects and features of the invention will be apparent from the claims.

The invention will now be described, by way of example, with reference to the accompanying drawings, in which.

The limb support shown in the Figures is principally intended for providing elevation/inclination, in use, to a patient's leg, and accordingly hereinafter the support will be described in relation to its use with a patient's leg, namely both the upper part above the knee and also the lower part of the leg beneath the knee down to and including the patient's foot.

In the embodiment shown in FIGS. 1 to 4, the limb support basically comprises four components, namely a base structure formed of a first fixed part 10 and a second adjustably movable part 11, and a support structure made up of a first support portion 12 for supporting a patient's foot and lower leg (calf), and a second support portion 13 for supporting the patient's thigh, i.e. portion of the patient's leg above the knee.

Although the base structure of the limb support of the invention could take various forms, the most important aspect of the base structure is that its length is adjustable so that, as will be described, altering its length alters the degree of elevation/inclination of the first and second support portions of the limb support.

Figure 1:
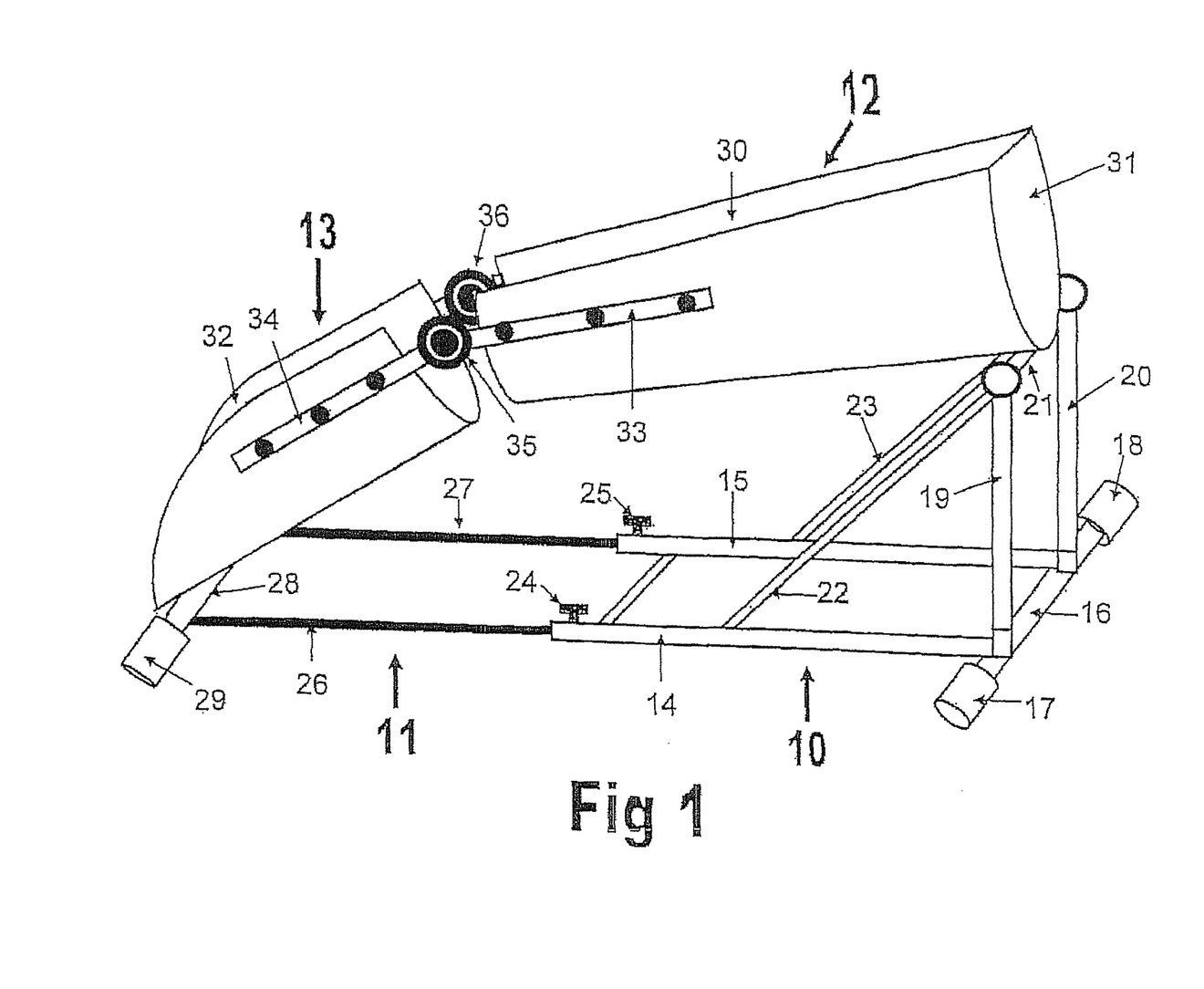
FIG. 1 is a schematic perspective view of a limb support of the invention in its partly extended form.

In the embodiment shown in FIG. 1, the first fixed part 10 of the base structure comprises a pair of straight hollow metal tubes 14, 15 respectively which are parallel and spaced apart. At one end the tubes are connected to a transverse crossbar 16 which is preferably of solid circular cross-section bar with respective cushion or rubber feet 17, 18 at the opposite ends thereof. The end of each tube can be connected to the crossbar 16 in any convenient manner, for example by welding. At the respective junctions of the tubes 14, 15 with the crossbar 16, are respective metal arms 19, 20 upstanding at 90° from the plane of the tubes 14, 15. Again these arms 19, 20 may be secured at said respective junction by any suitable means, such as welding. The arms, which are thus parallel to one another and spaced apart by the same spacing as that between the tubes 14, 15, have a crossbar 21 connected between the respective upper free ends of the arms 19, 20 and extending from the junction of the arms 19, 20 and the crossbar 21 at an angle downwardly onto the respective tubes 14, 15, are respective struts 22, 23 to provide rigidity to this fixed part 10 of the base structure. At the respective opposite ends of the tubes 14, 15 remote from the crossbar 16, the tubes are screw threaded to receive respective lock screws 24, 25. As will be described hereinafter, tightening or loosening of these lock screws secures or releases the part 11 of the base structure to or from the fixed part 10.

The part 11 of the base structure is formed of two parallel rods 26, 27 respectively which are of a cross-section and a size so that each can be slidingly received in a respective one of the tubes 14, 15, with the spacing apart of the rods being such as to allow this reception of them in the tubes 14, 15 as shown in FIG. 1. At the respective ends of the rods remote from the first fixed part 10 of the base structure, the rods are secured, for example by welding, to a transverse crossbar 28 of substantially the same form as the crossbar 16, the crossbar 28 having feet equivalent to the feet 17, 18 for the crossbar 16. One foot 29 is shown in FIG. 1. The feet on the crossbars 16 and 28 are intended to be received on a surface, in use, on which the limb support rests. Accordingly it will be understood that the lock screws 24, 25 can be manually rotated in opposite directions so as to tighten them down onto the portions of the rods 26, 27 within the tubes 14, 15 thereby locking the movable part 11 of the base structure relative to the fixed part 10 and thus fixing the length of the limb support base structure. If adjustment is required, as will be referred to hereinbelow, the lock nuts 24, 25 are loosened so that the movable part 11 can be slid further into the fixed part 10 or alternatively out of the fixed part 10, so as to shorten or lengthen the length of the base structure as required, this adjustment therefore taking place by virtue of the telescopic inter-engagement of the first part 10 and the movable part 11 of the base structure. It will be understood from the above that in this embodiment the adjustment is stepless. It is possible for the engagement of the end of each lock screw down onto the rod 26 or 27 to be sufficient to lock the adjusted movable part 11 in place. However alternatively some form of more positive locking could be provided, and alternatively the adjustment could be stepped, i.e. the rods 26, 27 could be provided with longitudinally spaced detents or the like into which the free ends of the lock screws engage in the locking position. Alternatively the rods 26, 27 could be replaced by hollow tubes which are provided with a series of longitudinally spaced apart openings in which the ends of the lock screws positively engage to provide the stepped adjustment.

In an alternative embodiment the lock nuts could be replaced by over-centre clamps or levers, providing a quick release/locking arrangement. In a further alternative embodiment the base structure could have a single telescopic rod and tube arrangement rather than rods 26, 27 and tubes 14, 15.

Although in the terms of the invention it would be possible for each of the support portions 12 and 13 to be basic supports for the portions of the patient's leg referred to above, for example in the form of flat boards or the like, the embodiment shown in the Figures provides each of the support portions in a form which is both open topped and internally contoured. By providing each support portion in effect in the form of a padded gutter, it is possible by making this gutter deep enough, effectively to control rotation and angulation.

Accordingly as seen in the embodiment of FIGS. 1 to 4, the first support portion 12 is of open-topped gutter form with internal padding denoted generally at 30, so that the inside of the gutter is contoured to receive therein and support the lower leg and foot of the patient, i.e. the portion of the patient's leg below the knee. As shown in the drawing, the end of the portion 12 at which the patient's foot is disposed in use, can be closed as at 31. However, is it preferable that this end is not closed because it is useful for a Doctor to be able to see a patient's foot at a glance in order to check for circulatory problems. The padding can be replaceable, so that different thicknesses can be provided for different sizes of limb. The padding can thus be a disposable item.

It can also be seen from FIGS. 1 to 4 that at the closed end 31 of the first support portion 12, the portion 12 is pivotally connected to the crossbar 21, this being by any convenient pivoting means. For example there could be a lower extension to the support portion 12 through which the crossbar 21 passes so that the support portion 12 can angularly move up and down on this cross bar 21. As shown in FIG. 1, the opposite end of the support portion 12 is open.

The second support portion 13 is very similar in construction to the first support portion 12, in that although it is shorter than the portion 12, and has, at its front, its opposite sides upwardly curved, it is again of open-topped gutter form with internal padding as denoted at 32. As shown in the drawings, it is open at both of its ends. As with support portion 12, the support portion padding can be replacable and thus disposable.

At its cut-away front end, the support portion 13 is, at its underside, pivotally connected to the crossbar 28. The pivotal connection can be of any convenient form and can, conveniently, be of the same form as the pivot between the support portion 12 and the crossbar 21.

As shown in FIGS. 1 to 4, the respective open ends of the first and second support portions are generally spaced apart, this being at the position, in use, which substantially corresponds to the position of the patient's knee joint. Correspondingly at this position the first and second support portions are pivotally connected together by any suitable pivot means.

In the example shown in the drawings, there are respective pivotal connections at opposite sides of the spacing between the two support portions. As can be seen from the drawing, the pivotal connection between the portions 12 and 13 at each side comprises respective links 33, 34 secured, for example by riveting, to respective sides of the support portion 12 and the support portion 13, the respective adjacent ends of the links each carrying a rotational part of the pivotal connection, these two rotational parts interlinking and inter-engaging to form a generally circular pivot as indicated at 35 for one side of the support portions 12 and 13, with the circular pivot 36 being shown at the opposite side.

The pivots 35 and 36 allow relative angular movement between the support portions 12 and 13 as the length of the base structure of the limb support is varied, and as a result the elevation of each of the support portions 12 and 13 is similarly adjusted so as to provide the correct elevation for the patient's leg.

Figure 2:
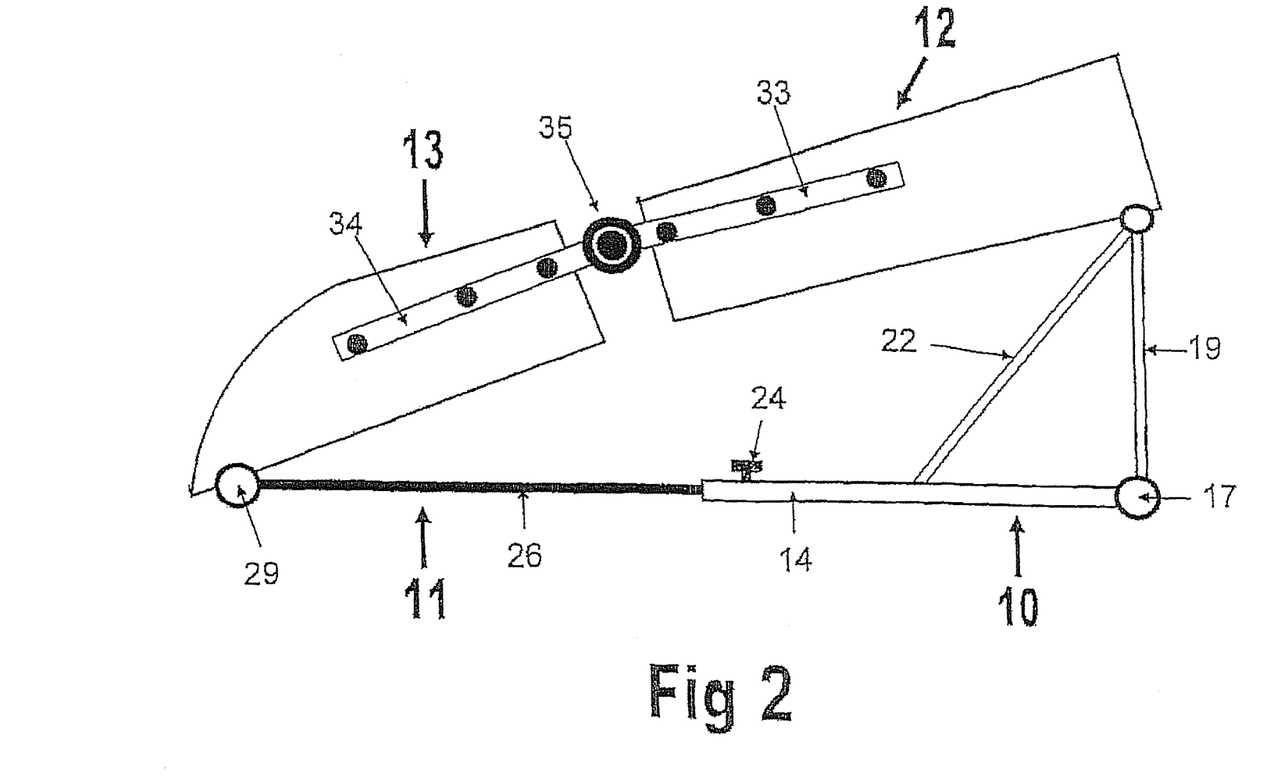
FIGS. 2 to 4 are side views of the limb support of FIG. 1 in its fully extended, partly retracted and further retracted forms respectively.

From the foregoing, it is believed apparent how the device operates in use. As described, the length of the base can be adjusted from the fully extended position shown generally in FIG. 2 where the first support portion 12 is in its extreme downwardly angled position, with the second support portion 13 being, in this state, substantially in line with the first support portion 12. This is reflected by the fact that, as shown in FIG. 2, the respective links 33, 34 associated with the circular pivot 35 are almost in line. In this position the patient's leg can be supported almost straight, with the thigh, i.e. the upper part of the leg above the knee, being received in the second support portion 13 and the lower part of the patient's leg (calf) and foot being received in the first support portion 12.

Figure 3:
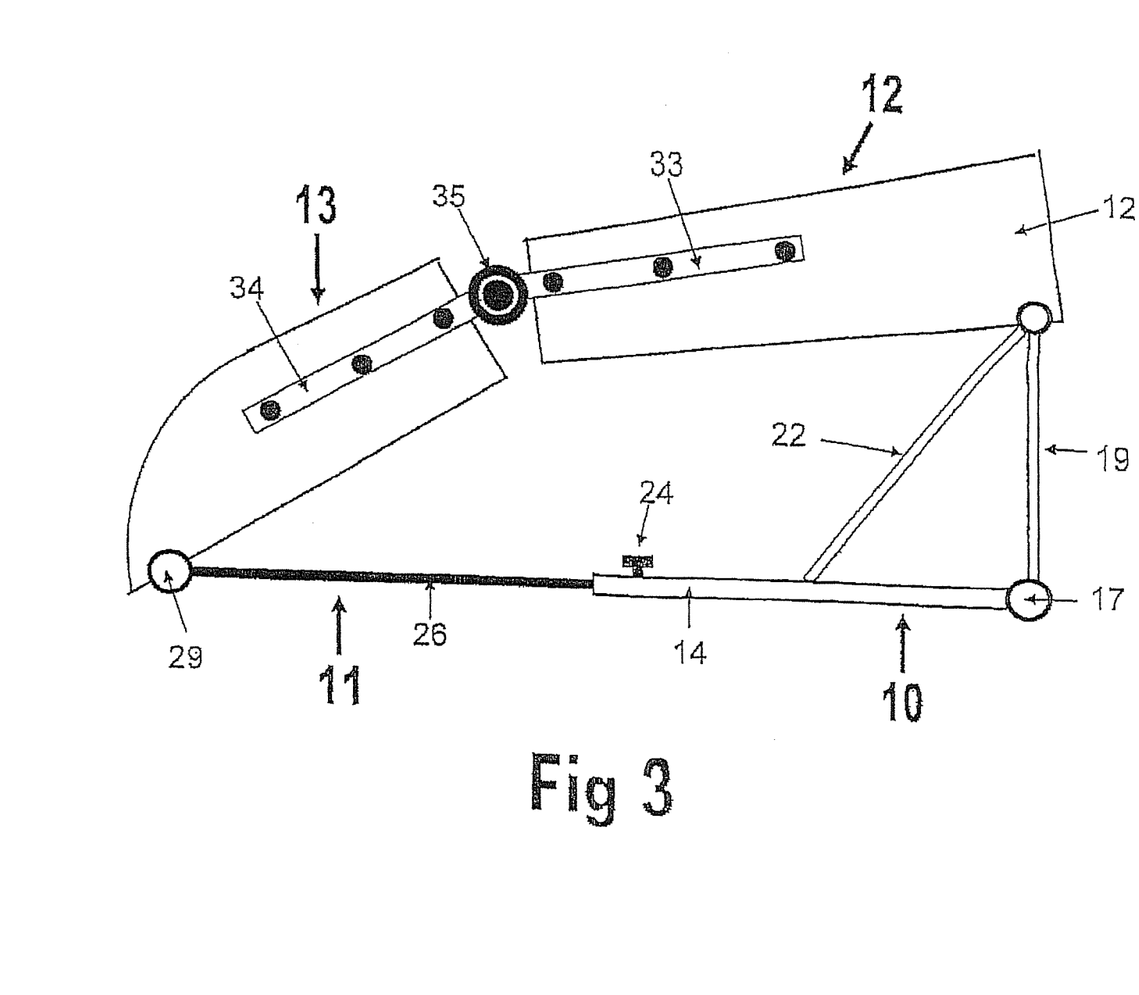
Figure 4:
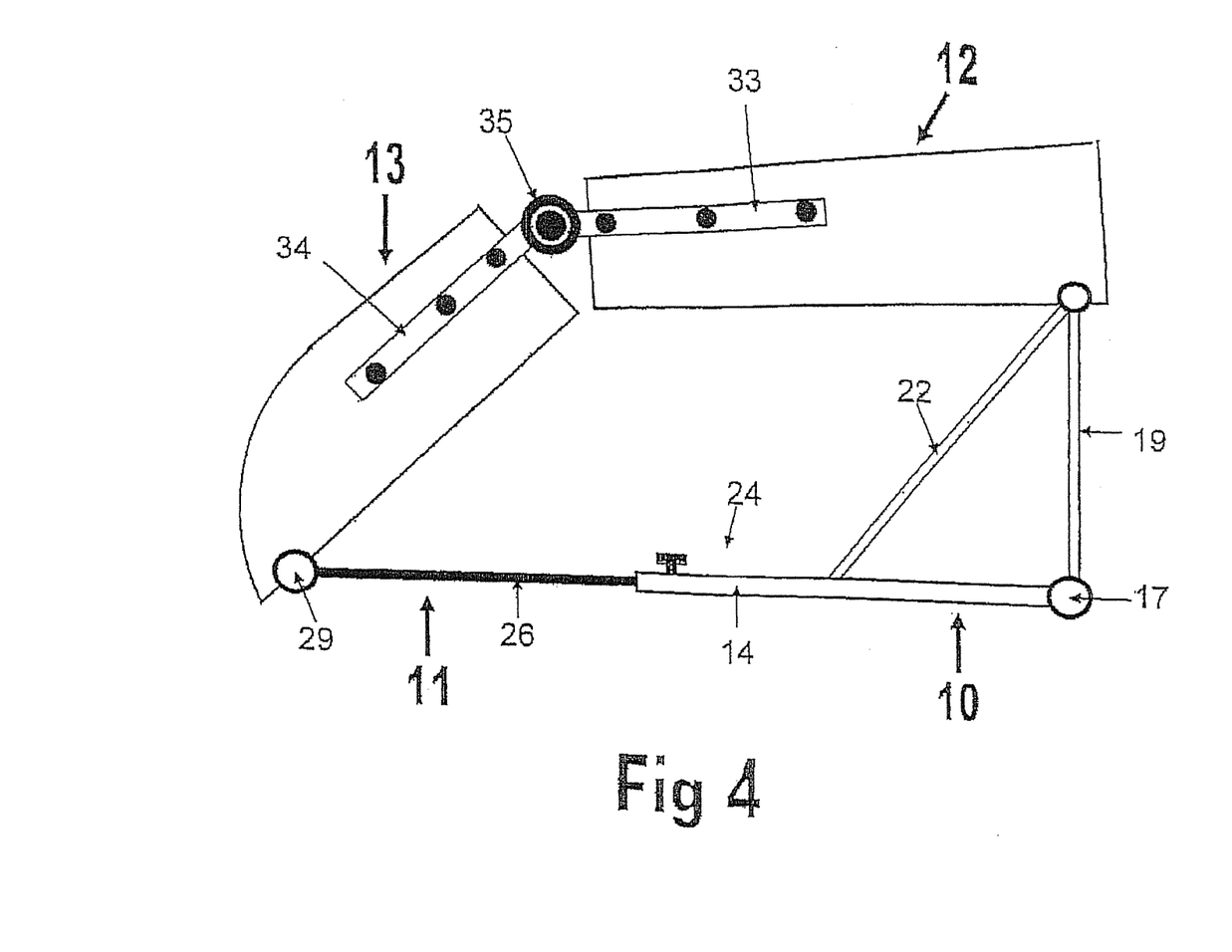

If however it is desired to alter the elevation/inclination of the patient's leg, the limb support is adjusted from its FIG. 2 position to for example, its FIG. 3 position by loosening the lock screws 24, 25 and sliding the part 11 of the base structure telescopically into the tubes 14, 15 until the FIG. 3 position is reached, where the length of the base structure is now reduced. This reduction in the length causes the upward pivoting of the second support portion 13 and a corresponding upward pivoting of the first support portion 12, with the results that the upper part of the patient's leg above the knee is now more elevated, whilst the lower part of the leg and foot is less angled. When in this adjusted position, the lock screws 24, 25 can be tightened to maintain the adjusted state. FIG. 4 shows a further adjusted position where the length of the base structure has been further reduced by untightening the lock screws and pushing the movable part 11 further into the tubes 14, 15 of the fixed part 10. As can be seen in FIG. 4, this further pivots the second support portion 13 upwardly in an anticlockwise direction, whilst the first support portion 12 pivots upwardly in a clockwise direction to bring it more to the horizontal, with the result that the elevation of the patient's upper leg part is increased still further.

Accordingly the limb support provided is in the form of a light-weight frame designed for the effective and comfortable support of a patient's leg in adjustable gradients of elevation. As stated, the lower leg and foot is supported in a padded gutter, which is deep enough effectively to control rotation and angulation. The adjustable hinge at knee level makes it possible to support the leg with the knee in variable degrees of flexion or in full extension. The support can be used in conjunction with a range of skin or skeletal traction options.

Figure 5:
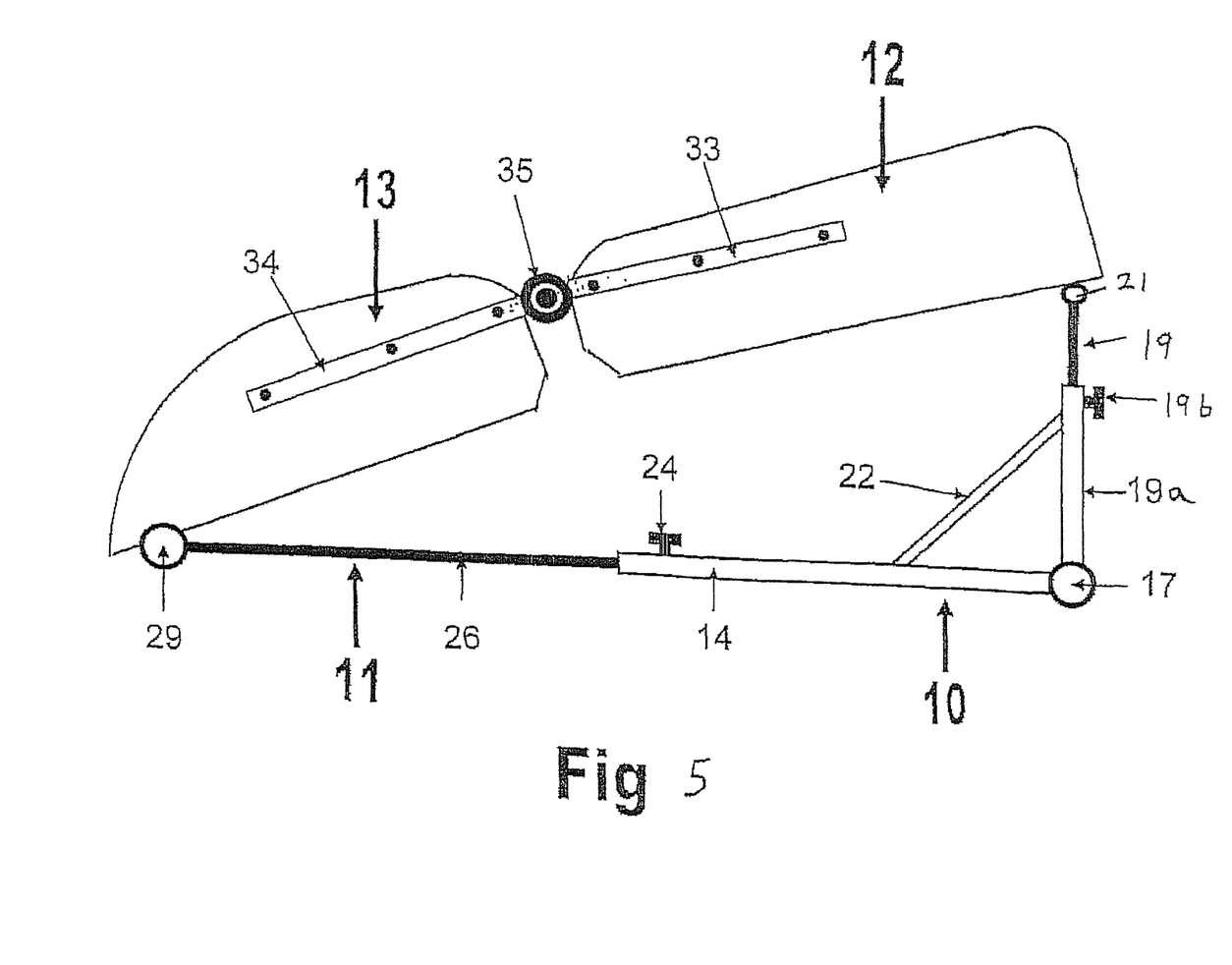
FIG. 5 is a view like FIG. 2, of an alternative embodiment of limb support.

In an alternative form of limb support, shown in FIG. 5, each arm 19, 20 is height adjustable. With the embodiment of FIGS. 1 to 4, adjustment of the angle between the thigh and calf parts by sliding rods 26, 27 in and out of tubes 14, 15 results in the gradient of the calf or thigh changing, whilst the height of the foot from the base structure remains constant. If the leg is held straight as in FIG. 2, there is a fixed gradient, as arms 19 and 20 are not adjustable. To be able to alter the height of the foot relative to the base structure, the arms 19, 20 are shown adjustable in FIG. 5.

Here the upper parts of arms 19, 20 are still connected to the crossbar 21, but their respective lower parts are telescopically slidable in respective hollow tubes upstanding from the transverse crossbar 16, with locknuts or over-centre clamps or levers to lock the arms in a height adjusted position. In FIG. 5, there is shown a hollow lower tube 19a in which the arm 19 can slide, and a lock nut 19b. The struts 22, 23 now extend from the tubes 14, 15 to the tops of the upstanding tubes 19a respectively.

Figure 6:
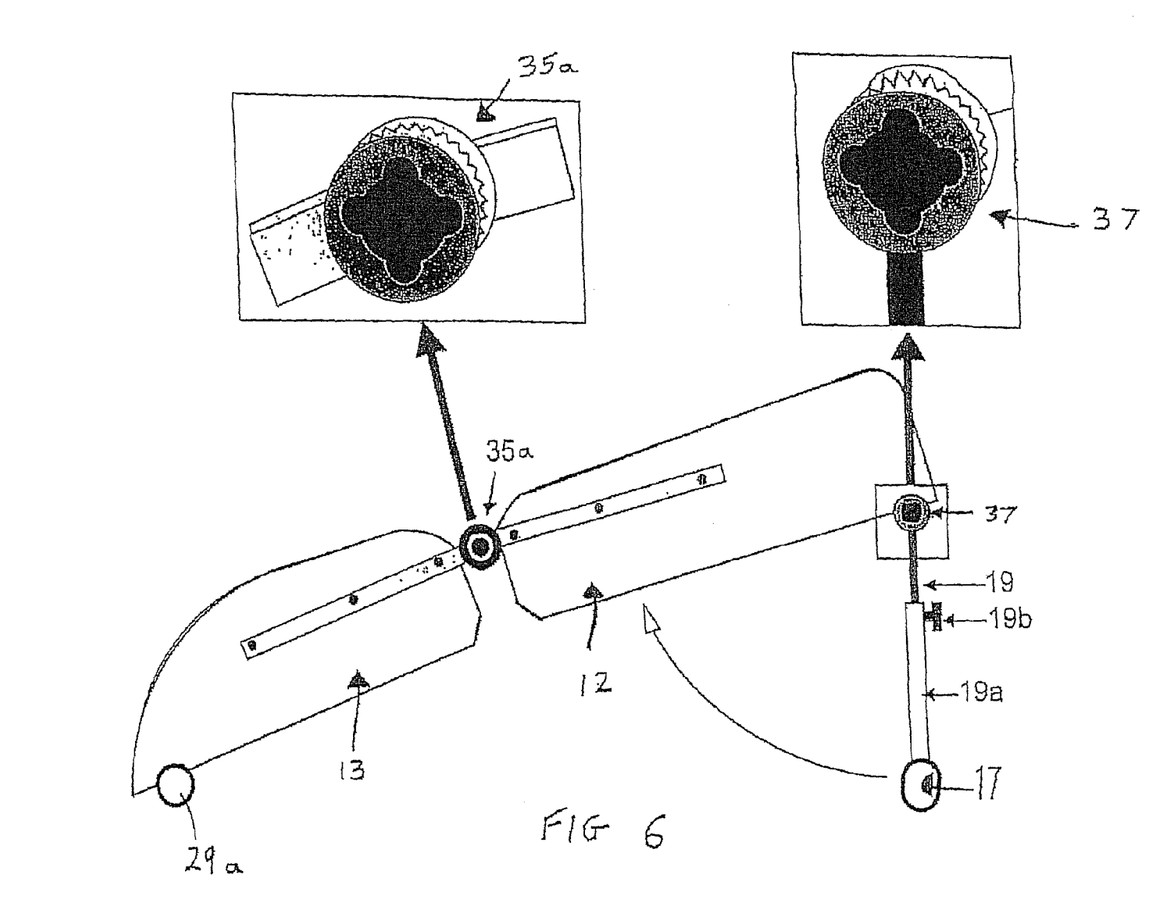
FIG. 6 is a view like FIG. 2 of a further embodiment of a limb support.

A different form of adjustable lower limb support is shown in FIG. 6. The main difference from the forms shown in FIGS. 1 to 4 and FIG. 5 respectively is that the pivots 35 and 36 are replaced by respective locking hinges, one of which 35a is shown, the hinges preferably being of a type manufactured by Sciel GmbH of Germany. By depressing a spring loaded button of the hinge the lock provided by interengaging teeth is released, allowing relative angular adjustment between the arms of the hinge, and thus between the first and second support portions 12 and 13 respectively. When the adjustment is complete, the button is released, and the hinge is locked, thereby fixing the portions 12 and 13 in a relatively adjusted chosen position.

The base structure is accordingly modified, comprising merely a first part to support the first support portion 12 and a separate, second part 29a to support the second support portion 13. Thus when the portions 12 and 13 are relatively adjusted as described, the two unconnected supports forming the base structure are merely moved relatively towards or away from one another appropriately.

As with the FIG. 5 embodiment, the support for portion 12 can be height adjustable, and preferably it is in the form of a tripod.

The connection at the crossbar to the portion 12 may also be by means of a locking hinge 37 or locking hinges, which could be set at a fixed position. The locking hinges 35a and 37 are shown as part of the limb support, and also separately to an enlarged scale, in FIG. 6. The support for portion 12 may be foldable about the hinge 37.

FIGS. 7 to 10 show a preferred form of a limb support of the invention. It comprises a first support portion 38 and a second support portion 39, having respective support functions equivalent to the portions 12 and 13 of the first three embodiments. However the first and second support portions of this embodiment are refined as compared to portions 12 and 13, in relation to improving support of the patient's leg.

Figure 7:
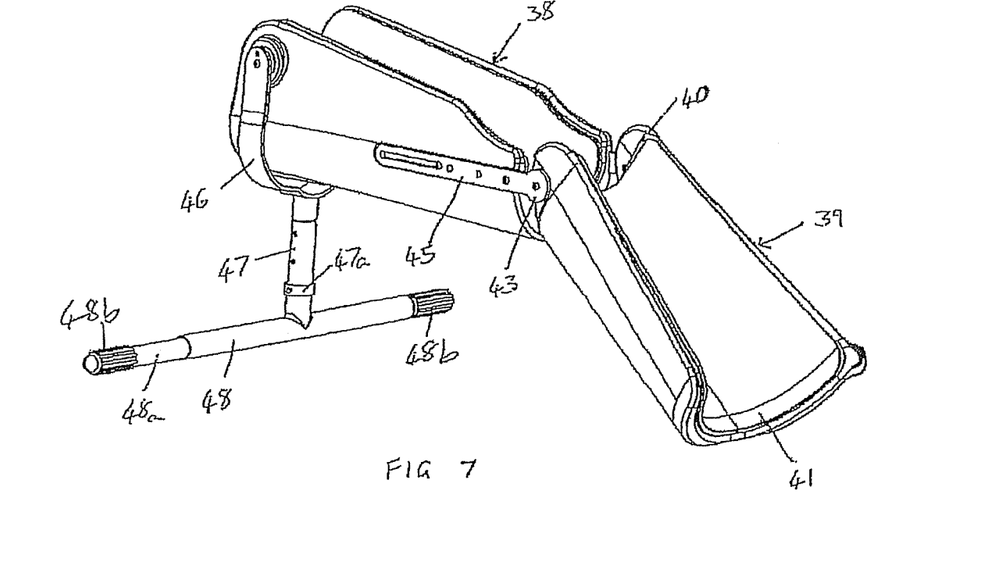
FIG. 7 is a view like FIG. 1, of a still further embodiment of a limb support.

Firstly, the second portion 39 is provided adjacent its end nearest the first portion with opposite internal side supports for the patients knee, one of which supports 40 is shown in FIG. 7. Secondly, the broader free end of the second portion has its edge tapered, as at 41, to accommodate the patient's thigh. Moreover at said end, the sides of the second portion are sloped down to reduce in height towards said tapered edge. It will be noted from FIG. 7 that there is no base support associated with the second portion, namely the underside of the free end thereof is intended to rest, in use, directly on the surface on which the limb support is positioned.

Figure 9:
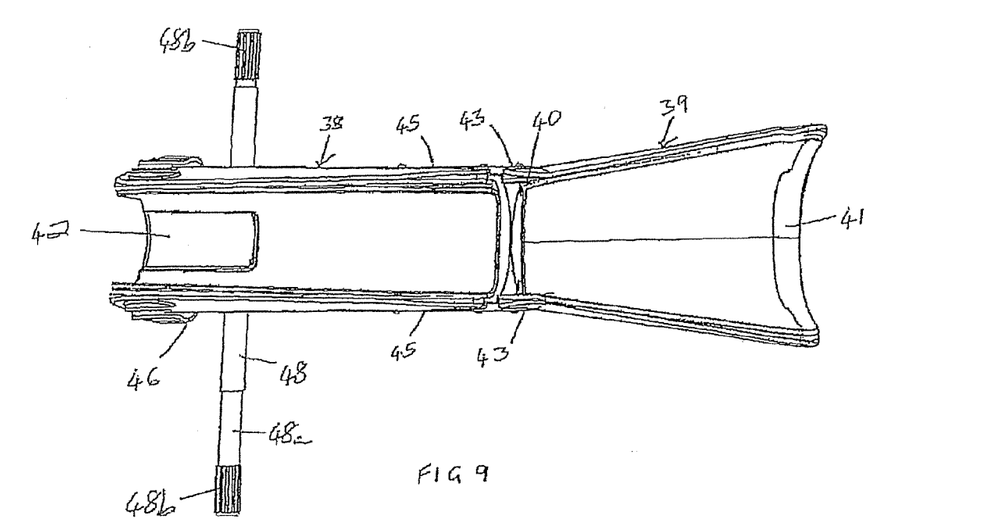
FIG. 9 is a top plan view of the embodiment of FIG. 7.
Figure 10:
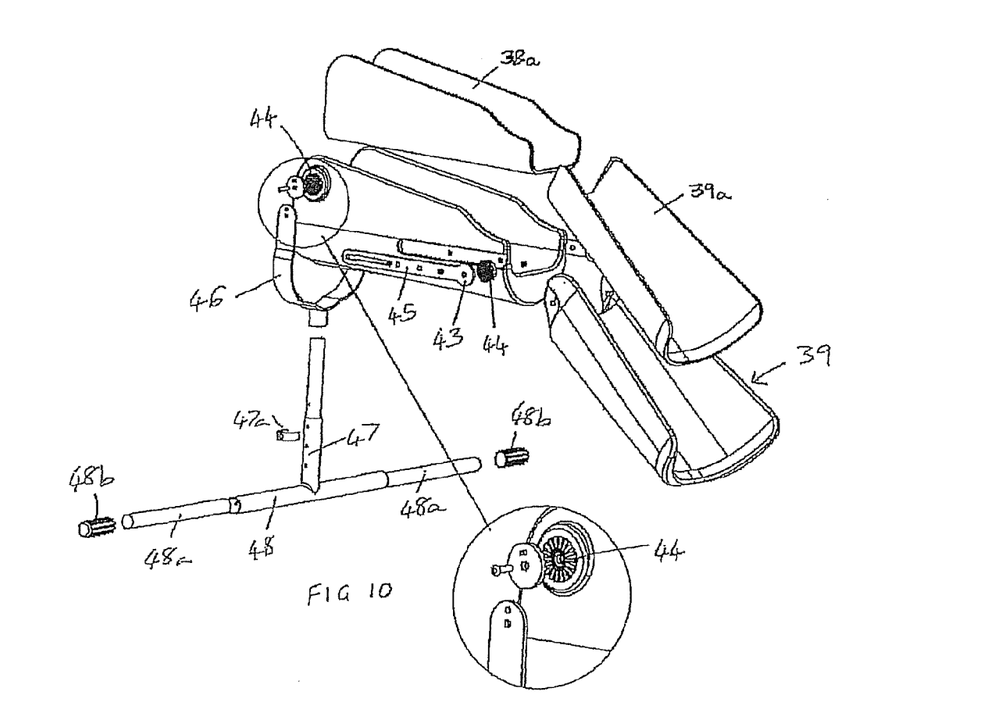
FIG. 10 is an exploded view of the embodiment of FIG. 7.

Thirdly, the first portion 38, adjacent its end furthest from the second portion, is centrally internally recessed as at 42 in FIG. 9, to accommodate, in use, the patient's heel. Fourthly, the end of the first portion 38 adjacent the heel recess 42 is open to allow a Doctor to easily see the patent's foot. Fifthly, the first portion 38, at its end adjacent its connection to the second portion, has its opposite sides reduced in height in order to accommodate, in use, a tibial or traction pin in the lower part of a patient's lower limb, i.e. at a position just below the knee. Sixthly, foam inserts 38a and 39a, as shown in FIG. 10, are provided to cushion the first and second portions 38, 39, respectively. These inserts 38a, 39a may be provided in a variety of sizes to suit different sized patients, for example, they may be 4 mm, 8 mm or 12 mm thick and may be made from polyethylene foam.

It is to be understood that appropriate ones of the refinements mentioned in respect of support portions 38 and 39 may be incorporated into the support portions 12 and 13 of the embodiments of FIGS. 1 to 4, FIG. 5, and FIG. 6, respectively.

Next with regard to the embodiment of FIGS. 7 to 10, it will be noted that the connection between the first and second support portions is different from that in the first two embodiments. FIG. 10 shows that adjustable locking hinge means at each side of each of the limb supports comprise first and second interengaging parts associated with the first and second support portions 38, 39 respectively. These interengaging parts comprise first and second interengaging castellated plates 43, 44 respectively. These are configured to allow angular adjustment in 20° increments. In the example shown, the plate 44 is secured to the exterior surface of the second support portion 39 at its narrower end, i.e. the end opposite that at which its edge is tapered.

Figure 8:
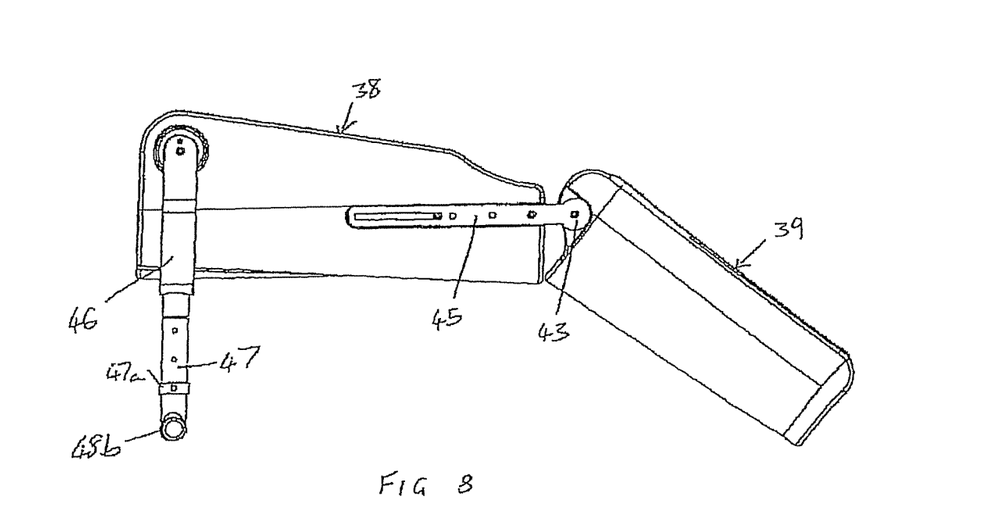
FIG. 8 is a side view of the embodiment of FIG. 7.

The plate 43 is, in this example, part of an adjustment bracket or link 45 connectible with the first support portion 38 to vary the distance between the first and second support portions 38, 39, as well as allowing for hinging between the two parts to alter the inclinations thereof. As shown in FIGS. 7, 8 and 10 the plate 43, which is at one end of the link 45, is of circular form, the remainder of the link 45 being straight and extending generally radially from the plate. This remainder of the link 45 is provided with longitudinally aligned spaced apertures selectively engageable with a peg on the exterior of the side of said first portion 38 to space apart the two support portions 38 and 39 as required. The exterior of the side of the first portion may be recessed to accommodate the link 45.

Various alternatives are possible. Firstly the plate 44 could also be part of a link 45 instead of, or in addition to, plate 43. Thus, either or both of the first or second portions 38, 39 may include adjustment means such as an adjustable link 45 to vary the separation of the two support portions 38, 39. Alternatively plate 43 need not be part of an adjustable link. Secondly, instead of being stepped, the adjustment could be stepless. Thirdly, locking means other than castellated plates could be used.

A pair of locking hinge means is preferably provided at respective opposite sides of the limb support (FIG. 9) to connect the first and second support portions together, but only the pair at one side is shown in FIGS. 7, 8 and 10.

Whereas the end support for the first portion 12 in the first three embodiments comprises a pair of spaced uprights, which may or may not be height adjustable, and on which the first portion is hinged, FIG. 7 shows a single support in the form of stirrup 46 carried by a base structure formed by a single central upright tube/column 47 fixed to a transverse foot bar 48, equivalent to crossbar 16. As shown, the upright 47 can be height adjustable, in a similar manner to arm 19 in tube 19a with lock nut 19b therebetween. However, as shown in this example, an e-clip 47a is provided to lock the height of the upright 47.

As shown in FIG. 7 the transverse foot bar 48 may be extendible by means of respective rods 48a telescopically engaged in each end of the bar 48. Extending the foot bar 48 increases the stability of the support. Knurled end caps 48b are attached to the respective free ends of the rods 48a to provide grip.

The stirrup 46 cradles the underside of the first support portion 38, and extends along opposite sides thereof. Its opposite free ends are connected to respective external sides of the first support portion 38 by means of respective adjustable locking hinges, which may, as shown, be of the type described in relation to plates 43, 44, namely utilising interengaging castellations. Thus one part of the locking hinge is fixed to the outside of the first support portion 38, whilst the other part is fixed to a free end of the stirrup 46. The first support portion 38 can thus be pivoted relative to the upright 47.

Instead of a single upright, there may be a pair of spaced uprights disposed symmetrically of the stirrup 46, each upright possibly being vertically adjustable.

Referring to FIGS. 11 to 14 there is shown a leg support 50 according to the invention comprising a first support portion 52, and a second support portion 54. (substantially equivalent to support portions 12 and 38, and 13 and 39 respectively in the earlier embodiments). The limb support further comprises a height adjuster 56. In this embodiment, preferably height adjuster 56 comes in two or more fixed heights and are therefore interchangeable in order to set the position of first support portion 52 above a surface (such as a bed).

In one form the first and second support portions are manufactured using rotational moulds for example using medium density polyetholeyne (MDPE). Beneficially, the material can comprise an anti-bacterial impregnation such as an active silver ingredient for example from Microban (registered trade mark) or Biocote (registered trade mark). In other forms, the first and second support portions are manufactured via thermo forming or thermostat formula processes, again, preferably comprising anti-bacterial impregnation.

Figure 12:
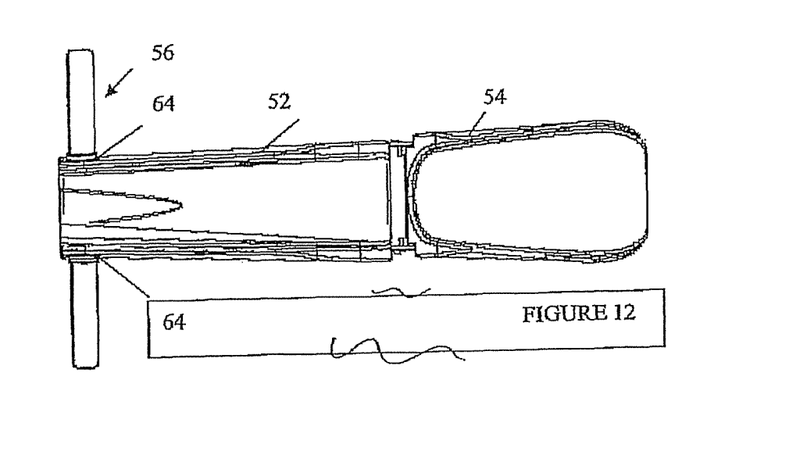
FIG. 12 is a plan view of the embodiment shown in FIG. 11.

Height adjuster 56 comprises a transversely extending foot portion 58, a vertical post 60 and a connecting portion 62 for connection to the first support portion 52 preferably at a hinge 64. Hinge 64 is most preferably a locking hinge similar to hinge 44 in FIG. 10. In an embodiment, connection portion 62 is U shaped and sized to accommodate the first support portion 52 and to connect thereto via two hinges 64 on each side of the first support portion 52 as can be seen in FIG. 12 for example.

Figure 11:
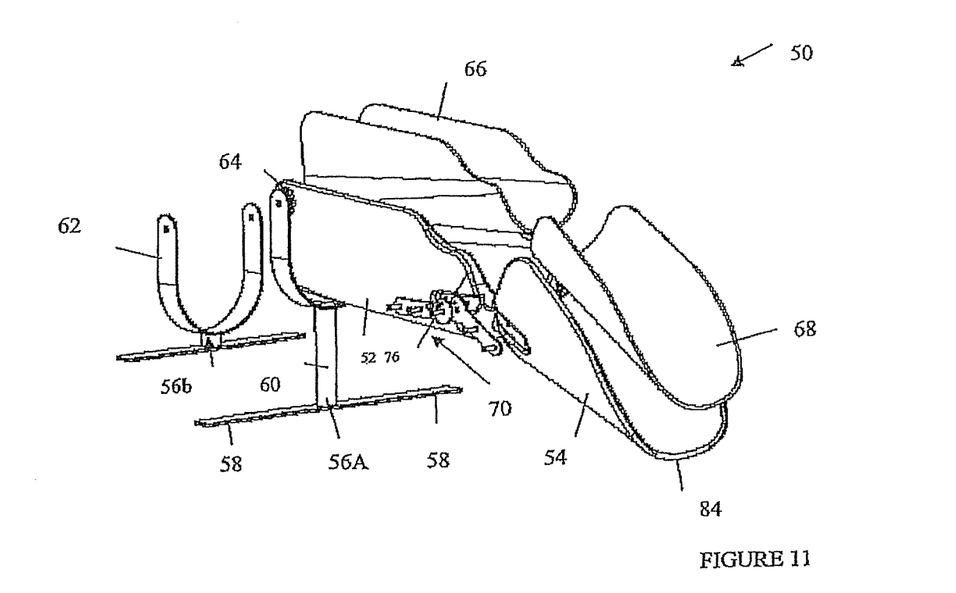
FIG. 11 is a schematic perspective view in exploded form of a further embodiment of a limb support according to the invention.

As can be seen in FIG. 11, two or more height adjusters 56 are preferably provided for a limb support 50 and here a first height adjuster 56a has a vertical post 60 approximately four times the length of post 60 on the second height adjuster 56b. For example, the height of post 60 of height adjuster 56a might be in the order of 10 to 20 cm and preferably in the order of 15 cm. The height of post 60 in embodiment 56b, might be in the order of 2 to 10 cm and preferably in the order of 6 cm. As can be seen, a patient's ankle sits fairly proximal the upper end of post 60 being separated only by the thickness of padding 66 the thickness of first limb support portion 52 and a small gap above the upper end of post 60.

Referring to FIG. 11, it can be seen that insertable padding portions 66 and 68 are provided. Preferably the padding inserts 66 and 68 are suitably shaped and contoured to nest well on the inside of first and second support portions 52 and 54 respectively. Beneficially the insertable padding 66 and 68 are disposable and can come in sizes to suit different types of patients, thereby incorporating thicker padding for thinner legs and thinner padding for larger legs.

Accordingly limb support 50 can come as a set of parts, comprising hinged first support portion 52 and second support portion 54 together with a range of height adjusters 56 and a selection of insertable padding 56 and 68.

Figure 13:
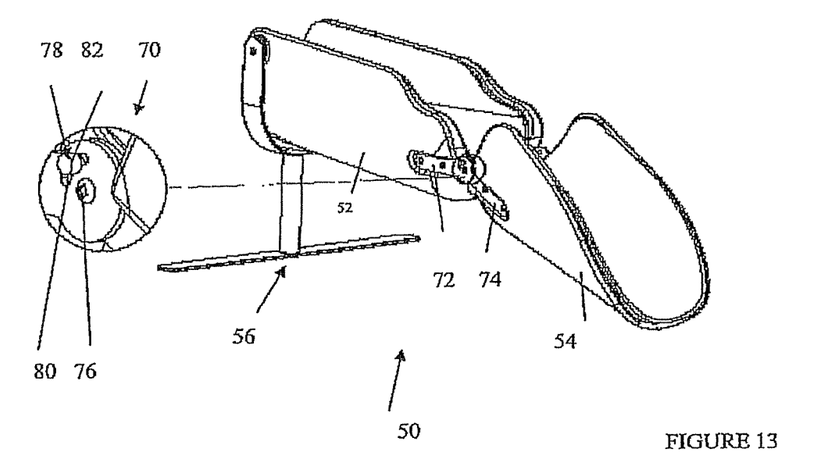
FIG. 13 is a perspective view of the embodiment shown in FIGS. 11 and 12 with a detail of the hinge mechanism.
Figure 14:
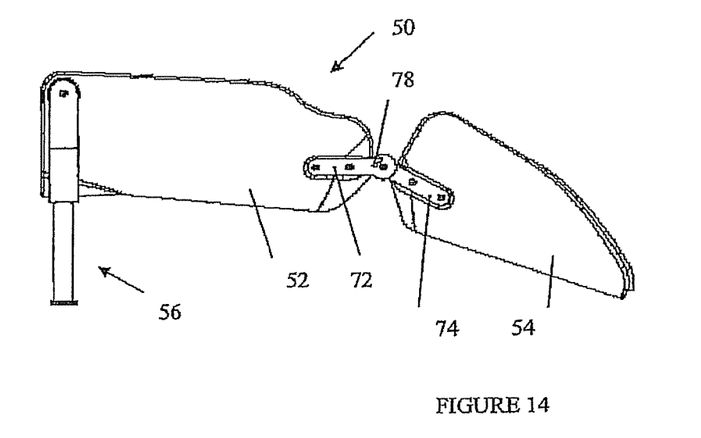
FIG. 14 is a side view of the embodiment shown in FIGS. 11, 12 and 13.

As in earlier embodiments, first support portion 52 and second support portion 54 are preferably hinged together to allow adjustment of the relative angle of the portions to one another. Referring to FIG. 13, an enlarged view of hinge 70 is shown. Preferably the hinge 70 comprises a first arm 72 attachable to first support portion 52 (recessed and attached eg screwed as in an earlier embodiment), and a second arm 74 attachable (in a recess and screwed or suitably fixed) to second support portion 54. Preferably the hinge comprises a central pivot 76 and also predetermined angle selector 78. In one form, arm 72 can comprise two or more tapped apertures adjacent to hinge 76 which enable a screw 82 to be inserted via a slot 80 enabling a patient carer, such as a nurse, to adjust the relative angle of first and second portions 52 and 54 by selecting the aperture in arm 72 fixing screw 82 into the selected tapped hole on each side of limb support 50 thereby rigidly to hold the first and second limb supports 52 and 54 at the selected angle. Beneficially, the screw 82 of the angle selector 78 is configured so as not to be removable from slot 80. In a preferred form, the tapped apertures in arm 72 are selected to enable the angle of inclination of first and second support portions 52 and 54 to be 0, 15° and 30°.

Accordingly, in use limb support 50 is configured from a set of parts to provide suitable lower limb support for a patient. To configure limb support 50, a carer needs to select suitable disposable insert 66 and 68 of appropriate dimensions for the predetermined patient. Additionally, the carer needs to select the height of elevation, based on clinical determination, and select from a choice of height adjusters 56. Additionally, the carer needs to select the relative angle of the first and second support portions 52 and 54 by adjusting the adjustment mechanism 78. Accordingly, in use the limb support 50 engages a surface by the foot 78 of height adjuster 56 and the lower edge 87 of second support system 54. The configuration of limb support 50 is determined by the angle selected by the carer at adjuster 58 and the selected height adjuster 56.

Beneficially, a stable limb support 50 is provided due to the length of foot 58 extending laterally from post 60 in the vertical height adjuster 56. Preferably, the width of the foot 58 at least the width of first leg support 52 on each side of the limb support 50, as can be seen in FIG. 12 for example. Accordingly, in one form the foot 58 has an overall width of approximately 50 cm. Moreover, beneficially a patient's leg is comfortably held by insertable padding 66 and 68 but nevertheless allows some movement of the limb within limb support 50. Such movement of a patient is accordingly stably supported by limb support 50 due to the configuration of foot 58 and the first and second support portions 52 and 54 respectively, in combination with other components of the limb support 50 described above. Moreover, the absence of the horizontal adjustment mechanism of the first embodiment shown in FIG. 1 for example above provides fewer components, and hence less complication in setting the limb support 50.

Although distinct embodiments have been described, it is to be understood that appropriate features from any one embodiment may be incorporated into another embodiment as required.

The invention claimed is:

1. A limb support for use with both a distal and a proximal part of a patient's lower limb comprising:
   a first portion for holding the distal part of the patient's lower limb;
   a second portion for holding the proximal part of the patient's lower limb;
   each portion having deep guttering which provides rotational and angulatory support to the relevant part of the limb;
   a support for supporting the distal part above a surface in use;
   said support having a stirrup with free ends opposite one another, each free end having a first adjustable locking hinge to opposite external sides of the first portion, said stirrups carried by a base structure resting on said surface in use;
   surface engaging portions comprising the support and free end of the second portion;
   and a second adjustable locking hinge connecting the first and second portions together, said first adjustable locking hinge comprises interengaging castellated plates.

2. A limb support according to claims 1 wherein each of the first and second portions is open-topped.

3. A limb support according to claim 2 wherein each of the first and second portions are contoured to support a lower and an upper parts of the patient's lower limb respectively.

4. A limb support according to claim 1 wherein each of the first and second portions are internally padded.

5. A limb support according to claim 4 wherein the padding is removable so that different thickness can be used for different sizes of limb, and preferably the padding is disposable.

6. A limb support according to claim 1 wherein the portions have a disposable cover thereon.

7. A limb support according to claim 1 wherein the second portion is provided internally with side support for the patient's knee.

8. A limb support according to claim 7 wherein the end of the second portion remote from its connection to the first portion has its edge tapered to accommodate the patient's thigh and wherein at said end, the sides of the second portion are sloped to reduce in height to said tapered edge.

9. A limb support according to claim 1 wherein the internal surface of the first portion is longitudinally centrally recessed to accommodate, in use, the patient's heel.

10. A limb support according to claim 1 wherein at the end of the first portion adjacent its connection to the second portion, the sides of the first portion are reduced to accommodate, in use, a tibial or traction pin in the lower part of the patient's lower limb.

11. A limb support according to claim 1 wherein the second adjustable locking hinge comprises first and second arms associated with the first and second portions respectively.

12. A limb support according to claim 1 wherein said first adjustable locking hinge comprises first and second interengaging castellated plates, wherein each of said first and second interengaging castellated plates is fixed each of opposing external sides said first portion, at the distal end of said first portion opposite said second adjustable locking hinge.

13. A limb support according to claim 1 wherein said second adjustable locking hinge comprises first and second arms provided at opposing external sides of the limb support wherein said first and second arms connecting said first portion and said second portion.

14. A limb support according to claim 1 wherein the base structure is vertically adjustable.

15. A limb support according to claim 1 wherein the base structure comprises a single adjustable post extending vertically downward centrally of said stirrup away from said free ends of said stirrup.

16. A limb support according to claim 15 wherein said single adjustable post terminates to a transverse foot bar.

* * * * *